United States Patent
Kinnunen et al.

(10) Patent No.: US 10,507,358 B2
(45) Date of Patent: Dec. 17, 2019

(54) ANALYZING PHYSIOLOGICAL STATE FOR FITNESS EXERCISE

(75) Inventors: Hannu Kinnunen, Oulu (FI); Jarkko Haataja, Tuusula (FI); Tero Posio, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 1373 days.

(21) Appl. No.: 13/177,610

(22) Filed: Jul. 7, 2011

(65) Prior Publication Data

US 2012/0010478 A1 Jan. 12, 2012

(30) Foreign Application Priority Data

Jul. 12, 2010 (FI) .................................. 20105796

(51) Int. Cl.
*A61B 5/0205* (2006.01)
*A63B 24/00* (2006.01)
(Continued)

(52) U.S. Cl.
CPC ...... *A63B 24/0062* (2013.01); *A61B 5/02405* (2013.01); *A61B 5/222* (2013.01); *G06F 19/3481* (2013.01); *G09B 19/0038* (2013.01); *A61B 5/02438* (2013.01); *A61B 2503/10* (2013.01); *A63B 22/02* (2013.01); *A63B 22/0605* (2013.01); *A63B 2024/0065* (2013.01); *A63B 2024/0068* (2013.01); *A63B 2071/0655* (2013.01); *A63B 2071/0663* (2013.01);
(Continued)

(58) Field of Classification Search
CPC ............................ A61B 5/02405; A61B 5/222
See application file for complete search history.

(56) References Cited

U.S. PATENT DOCUMENTS 6,026,320 A * 2/2000 Carlson .................. A61N 1/365
600/510
6,104,947 A * 8/2000 Heikkila .............. A61B 5/0245
600/519
(Continued)

OTHER PUBLICATIONS

Martin Schindler, European Search Report for corresponding European Patent Application No. EP11172618, pp. 1-2 (dated Oct. 25, 2012).
Communication from EPO for corresponding European Patent Application No. EP11172618.8, pp. 1-4 (dated Jul. 22, 2014).
Jesper Lundbom, Finnish Search Report for corresponding Finnish Application No. 20105796, p. 1, dated May 11, 2011.

*Primary Examiner* — Carl H Layno
*Assistant Examiner* — Jennifer L Ghand
(74) *Attorney, Agent, or Firm* — FisherBroyles, LLP

(57) ABSTRACT

A method, apparatus, and a computer program for monitoring a fitness exercise are described. A plurality of heart-rate variability values and a plurality of exertion parameter values are measured during an exercise measured. The heart rate variability values correlate with the exertion parameter values through a human physiological mechanism, and the exertion parameter values characterize the physical exertion of the exercise. A mathematical correspondence is then constructed from the plurality of measured heart rate variability values and associated exertion parameter values. The mathematical correspondence describes correlation between the heart rate variability values and the exertion parameter values and the user's physiological state during the exercise. Then, the physical exertion of the exercise is monitored by applying the mathematical correspondence.

12 Claims, 3 Drawing Sheets

(51) Int. Cl.
  *A61B 5/024*   (2006.01)
  *A61B 5/22*    (2006.01)
  *G09B 19/00*   (2006.01)
  *G06F 19/00*   (2018.01)
  *A63B 22/02*   (2006.01)
  *A63B 22/06*   (2006.01)
  *A63B 71/06*   (2006.01)

(52) U.S. Cl.
  CPC ....... *A63B 2220/12* (2013.01); *A63B 2220/30* (2013.01); *A63B 2220/836* (2013.01); *A63B 2225/20* (2013.01); *A63B 2225/50* (2013.01); *A63B 2230/04* (2013.01); *A63B 2230/06* (2013.01); *A63B 2230/75* (2013.01)

(56) References Cited

U.S. PATENT DOCUMENTS

| | | | |
|---|---|---|---|
| 2001/0027266 A1* | 10/2001 | Hautala | A61B 5/222 600/16 |
| 2006/0032315 A1 | 2/2006 | Saalastic et al. | |
| 2007/0082789 A1 | 4/2007 | Nissila et al. | |
| 2007/0249467 A1 | 10/2007 | Hong et al. | |
| 2008/0214359 A1* | 9/2008 | Niva | A63B 71/06 482/9 |
| 2009/0156944 A1 | 6/2009 | Kinnunen et al. | |

\* cited by examiner

ANALYZING PHYSIOLOGICAL STATE FOR FITNESS EXERCISE

CROSS-REFERENCE TO RELATED APPLICATION

This application claims priority based on Finnish Application No. 20105796, filed Jul. 12, 2010, which is incorporated herein by reference.

BACKGROUND

Field

The invention relates to the field of biometric sensing and, particularly to measuring a physiological state of a person for fitness exercise.

Description of the Related Art

Heart-rate monitors and other biometric sensors are commonly used by professional athletes as well as by amateurs practicing exercising. Heart-rate monitors and other biometric sensors typically provide a user with information enabling efficient workout. A typical heart-rate monitoring system includes a biometric sensor attached to the body of the user and configured to measure heart rate of the user, to transmit the measured heart-rate to another device worn by the user (a wrist device, for example). The prior art also teaches systems where the wrist device itself includes the biometric sensor. The heart-rate information obtained with the biometric sensor is processed and displayed to the user. More advanced information, such as energy expenditure and fitness parameters of the user may also be calculated from the heart rate.

In heart rate monitoring, an aspect is to provide the user with information on the appropriate exertion level of an exercise. The exertion levels are typically characterized with heart rate zones, which tell the user appropriate values of heart rate at which the desired training response is achieved. The heart rate zones may be used for post-analysis of the exercise. In such case, the quality of the exercise is assessed in terms of how heart rate has accumulated at each heart rate zone. Furthermore, the estimated response to exercise is reported to the user. For example, if the heart rate primarily falls to the lower heart rate zones, the apparatus may indicate that the training effect was primarily associated with fat burning instead of improving fitness. If the exercise was carried out at higher heart rate zones, the apparatus may tell the user that the exercise was to improve maximum capacity. The heart rate zones may further be used as guiding tools during exercise. In such a case, the apparatus may show the user the currently used zone. The apparatus may show the user the target value for the accumulated time at each heart rate zone, and the user may change the exertion level such that the targets are fulfilled.

The user's adaptation capability to an exercise may vary between days, and therefore the user may benefit from day-specific exertion zones. Therefore, it is useful to consider alternative techniques to determine exertion zones for an exercise.

SUMMARY

According to an aspect of the present invention, there is provided an apparatus for processing exercise-related measurement data, comprising a processor configured to cause the apparatus to: acquire a plurality of heart rate variability values and a plurality of exertion parameter values measured during an exercise, wherein the heart rate variability values correlate with the exertion parameter values through a human physiological mechanism, and wherein the exertion parameter values characterize the physical exertion of the exercise; construct a mathematical correspondence from the plurality of measured heart rate variability values and associated exertion parameter values, the mathematical correspondence describing correlation between the heart rate variability values and the exertion parameter values and describing the user's physiological state during the exercise; and monitor the physical exertion of the exercise by applying the mathematical correspondence.

According to another aspect of the present invention, there is provided a computer program product embodied on a non-transitory distribution medium and comprising a set of computer program instructions configuring, when executed in a processor, said processor to execute a computer process comprising: acquiring a plurality of heart rate variability values and a plurality of exertion parameter values measured during an exercise, wherein the heart rate variability values correlate with the exertion parameter values through a human physiological mechanism, and wherein the exertion parameter values characterize the physical exertion of the exercise; constructing a mathematical correspondence from the plurality of measured heart rate variability values and associated exertion parameter values, the mathematical correspondence describing correlation between the heart rate variability values and the exertion parameter values and describing the user's physiological state during the exercise; and monitoring the physical exertion of the exercise by applying the mathematical correspondence.

According to yet another aspect of the present invention, there is provided a method for processing exercise-related measurement data in an apparatus. The method comprises acquiring a plurality of heart rate variability values and a plurality of exertion parameter values measured during an exercise, wherein the heart rate variability values correlate with the exertion parameter values through a human physiological mechanism, and wherein the exertion parameter values characterize the physical exertion of the exercise. The method further comprises constructing a mathematical correspondence from the plurality of measured heart rate variability values and associated exertion parameter values, the mathematical correspondence describing correlation between the heart rate variability values and the exertion parameter values and describing the user's physiological state during the exercise. Then, the physical exertion of the exercise is monitored by applying the mathematical correspondence.

In an embodiment of the method, monitoring the physical exertion of the exercise comprises adapting ranges of a plurality of exertion level zones of the exercise to the mathematical correspondence, wherein the ranges of the exertion level zones are defined as exertion parameter values. In an embodiment, adapting the ranges of the exertion level zones further comprises: acquiring an exertion parameter value associated with a predetermined heart rate variability value through the mathematical correspondence; and setting the exertion parameter value as an upper limit or a lower limit of an exertion level zone. In a further embodiment, the method further comprises initializing an exercise profile comprising a plurality of said exertion level zones with different ranges defined as initial values of the exertion parameter values, and changing a range of at least one exertion level zone by changing at least one initial value of the exertion parameter value of said at least one exertion level zone on the basis of the constructed mathematical correspondence. In an embodiment, it is determined for each exertion level zone a factor characterizing a training effect at that exertion level zone in the current physiological state of the user, wherein said factor for each exertion level zone is derived from said mathematical correspondence. In an embodiment, the method further comprises displaying at least one range of a plurality of exertion level zones to the user.

In an embodiment of the method, said exertion parameter includes at least one of the following exertion parameters: heart rate, speed of motion, pedaling power, and motion intensity.

In an embodiment of the method, constructing the mathematical correspondence further comprises: providing a plurality of different candidate mathematical correspondence models; determining correlation between the acquired heart-rate variability values and said plurality of different candidate mathematical correspondence models; and selecting a mathematical correspondence model having the highest correlation with the acquired heart-rate variability values.

In an embodiment of the method, the method further comprises: inputting an exertion parameter value; and displaying the exertion parameter value to the user along with a reference exertion parameter value obtained from the mathematical correspondence.

In an embodiment of the method, controlling the apparatus to monitor the physical exertion of the exercise comprises: determining a target heart rate variability value or a target heart rate variability range for the exercise; obtaining, from the mathematical correspondence, a target exertion parameter level or range corresponding to the target heart rate variability value or range; and instructing the user to achieve the target exertion parameter level or range.

According to yet another aspect of the present invention, there is provided a computer program product embodied on a computer-readable distribution medium and comprising program instructions for carrying out the above-described method. According to another aspect, there is provided a computer-readable distribution medium or article of manufacture containing the above-mentioned computer program product.

According to yet another aspect of the present invention, there is provided an apparatus comprising means for carrying out the above-described method or any one of above-described embodiments.

Further embodiments of the invention are defined in the dependent claims.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Further, words "comprising" and "including" are to be understood not to limit described embodiments to consist only those features that are actually described. Instead, the described embodiments may include other features and/or components that have not been specifically mentioned.

Figure 1:
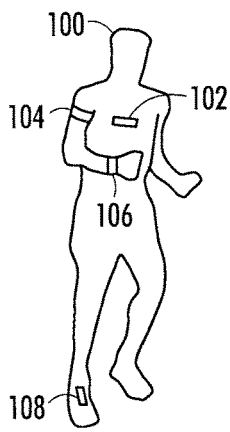
FIG. 1 illustrates a system for measuring and processing exercise-related information.

FIG. 1 illustrates an exemplary system for use in connection with embodiments of the present invention. The system is used to measure exercise-related data in order to monitor workout of a user 100. Referring to FIG. 1, the user may wear various devices that measure and process the exercise-related data. The user 100 is provided with the following equipment: a user interface apparatus 106 in the form of a wrist unit, a heart activity sensor 102 worn on the chest of the user 100, an upper-arm-mounted positioning device 104, and a shoe-mounted stride sensor 108. Other accessories not illustrated in FIG. 1 include a bike sensor configured to measure the speed of a bike and/or a pedaling power of the user, a swimming sensor configured to monitor swimming motions, water pressure etc., and other devices not worn by the user but connected to an exercise apparatus (e.g. an exercise bicycle and a treadmill) and measuring exercise-related parameters. The accessory devices 102, 104, 108 communicate wirelessly with the user interface apparatus 106. Various accessory devices 102, 104, 108 may be flexibly used as needed, i.e. all of them are not necessarily needed all the time, or by all users, or in all use cases.

The user interface apparatus 106 comprises a user interface which may comprise a display, means for producing sound, a keyboard, and/or a keypad. The display may be a liquid crystal display, for example, but it may also be implemented by any appropriate technique. The display may also incorporate other user interaction means, such as touch input, or haptic feedback, i.e. the display may be a touch screen. The means for producing sound may be a loudspeaker or a simpler means, such as a piezo element, for producing beeps or other audio signals. The keyboard/keypad may comprise a complete (QWERTY) keyboard, a mere numeric keypad or only a few push buttons and/or rotary buttons. In addition, the user interface 106 may comprise other prior art user interface elements, for example various means for focusing a cursor (mouse, track ball, various arrow keys, touch sensitive area etc.) or elements enabling audio control. A parameter relating to the exercise may be shown on the user interface 106, on the display, for example. The shown parameter may comprise an instruction to guide the exercise, or it may illustrate a training effect of the exercise. The user interface device 106 also comprises means for communicating wirelessly with the accessory devices 102, 104, and 108, as described in greater detail below.

The heart activity sensor 102 is used for measuring the user's heart activity. The heart activity comprises heart rate and one or multichannel EKG (Electrocardiogram), for example. The heart activity sensor 102 may further measure other physiological parameters that can be measured from the user. There exist various wireless heart rate monitoring concepts where a heart rate sensor attached to the user's chest measures the user's heart activity and transmits associated heart activity data telemetrically to a heart rate receiver, such as the user interface apparatus 106, e.g. the wrist device attached to the user's wrist. The transmission of the heart activity data may utilize the principles of time division and/or packet transmission, for example. The heart rate sensor may be used to determine exertion of an exercise in terms of the heart rate of the user.

The positioning device 104 receives external location information. The positioning device 104 may be a receiver of a global navigation satellite system. Such a system may be the Global Positioning System (GPS), the Global Navigation Satellite System (GLONASS), the Galileo Positioning System (Galileo), the Beidou Navigation System, or the Indian Regional Navigational Satellite System (IRNSS), for example. The positioning device 104 determines its location elements, such as longitude, latitude, and altitude, using signals transmitted from satellites orbiting the earth. The positioning device 104 may be used to determine the location and the exertion of an exercise in terms of the speed of the user.

The stride sensor 108 (or the swimming sensor) comprises one or more motion sensors measuring the movement of the user, a processing unit configured to process the measured motion data of the user and to transmit the processed data to the user interface apparatus 106 over a wireless connection. Examples of suitable motion sensors include: Analog Devices ADXL105, Pewatron HW or VTI Technologies SCA series. The implementation of the accelerometer may also be based on other appropriate techniques. The stride sensor 108 may be used to determine the exertion of an exercise in terms of the speed or number of strides per time unit. Accelerometers may also be integrated into the heart activity sensor 102 and/or the user interface apparatus 106.

Figure 2:
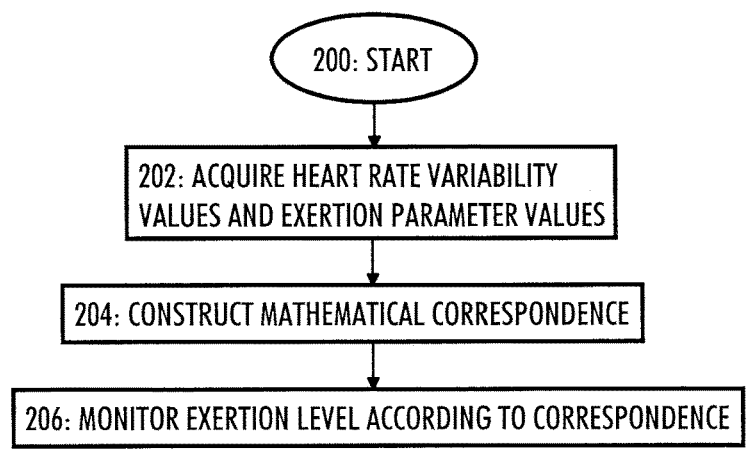
FIG. 2 is a flow diagram of a process for determining exercise parameters according to an embodiment of the invention.

FIG. 2 is a flow diagram illustrating a method for processing exercise-related measurement data in an apparatus according to an embodiment of the invention. Referring to FIG. 2, the process starts in block 200, and a plurality of heart rate variability (HRV) values and a plurality of exertion parameter values are acquired in block 202. The heart rate variability is a measure of variation in heart beat intervals, also called R-R intervals. The heart rate variability may be interpreted as a measure of the prevailing physiological state of an individual. Particularly, the heart rate variability characterizes the state of the user's sympathetic and parasympathetic neural systems. The HRV values are preferably measured during an exercise, e.g. in the beginning of the exercise, wherein the heart-rate variability values are measured as a function of the exertion parameter values correlating with the heat-rate variability through human physiological mechanism and, thereby, each heart-rate variability value is associated with a different value of the exertion parameter value. In principle, the exertion parameter may be any metric that can be used to define the exertion level of the exercise and that has correlation with the HRV, e.g. the heart rate, cycling cadence, speed, force, pedaling power, and/or motion intensity.

In block 204, a mathematical correspondence is constructed from the plurality of measured HRV values and associated exertion parameter values, the mathematical correspondence describing a correlation between the heart-rate variability and the exertion parameter values and, as a consequence, describing the user's current physiological state. The mathematical correspondence may be a mathematical model that provides a sufficient match with the pattern of HRV values as the function of the exertion parameter values. Therefore, the mathematical correspondence may be a function describing the dependence of the HRV on the exertion or, in general terms, correlation between the HRV and the exertion. Alternatively, the mathematical correspondence may be built to describe the dependence of the exertion on the HRV. In block 206, the exertion level of the exercise is monitored according to the mathematical correspondence constructed in block 204. In an embodiment, block 206 comprises adapting ranges of a plurality of exertion level zones of the exercise to the constructed mathematical correspondence, wherein the ranges of the exertion level zones are defined as values of the exertion parameter. The exertion level zones may then be used to guide the user according to an exercise profile defined by a pattern of exertion level zones. In another embodiment, block 206 comprises monitoring the training effect of the exercise.

As embodiments of the present invention utilize a plurality of HRV values with different values of the exertion parameter, the embodiments are able to construct an accurate mathematical correspondence or model of the dependence between the HRV and the exertion. The mathematical correspondence may also be used to describe the correlation between the heart rate variability and the exertion for heart rate variability values other than said measured heart rate variability values. In other words, the mathematical correspondence may be used to determine, e.g. by interpolating or extrapolating, the value of the exertion parameter where the heart rate variability has a determined value, e.g. 1 ms, even though the measurements did not include HRV of 1 ms. This enables the determination at which values (or range) of the exertion parameter value a desired physiological response, as described by the HRV values, is obtained. The model may then be used to derive the user's prevailing physiological state and to select the exertion level zone limits to match with the physiological state so that the user experiences a desired training effect during the exercise. For example, when the user is well rested the effect of improved aerobic fitness may be obtained with heart rates between 140 to 160 pulses per minute. On the other hand, when the user is exhausted as a result of a massive exercise on the previous day, the effect of improved aerobic fitness may be obtained with heart rates between 125 to 145 pulses per minute. The physiological state of the user is affected by the amount of training on the previous days, the amount and quality of sleep, stress, etc., and the physiological state is measured and processed accurately with the embodiments of the invention so that the exertion level of the exercise may be adapted to the measured physiological state so as to achieve the desired training effect or to determine the physiological effect of the exercise. The physiological state maps directly to the HRV.

As mentioned above, the exertion level may be adapted not only to the heart rate but also to any metric that may be measured and which has the correlation with the exertion level. Such an exertion parameter may be any exertion parameter measured with accessory apparatuses 102, 104, and 108, each comprising at least one measurement sensor which measures some aspect of the exercise correlating with the exertion of the exercise. In addition to said wearable accessory apparatuses, the exertion level of the exercise may be determined with a speed/cadence sensor attached to pedals of a bicycle (or exercise cycle) and/or with corresponding sensors attached to other common exercising instruments. Heart rate zones may be used as means for guiding the exertion level of the exercise and an exercise profile. In principle, the same analogy of guiding the exertion level of the exercise may be expanded to other parameters obtained from the sensors of the accessory devices mentioned above, e.g. the pedaling power and the speed. For example, the HRV values may be acquired with different heart rates in block 202, and the mathematical correspondence constructed in block 204 is the correspondence between the HRV and the heart rate. In an embodiment, at least some of the HRV values are calculated at heart rates between 80 and 120 pulses per minute so that the mathematical correspondence is accurate also at lower heart rates. The exertion levels adapted in block 206 are then the limits of the heart rate zones of the exercise. Analogously, the HRV values may be acquired with different running speeds (measured by a stride sensor or positioning system) in block 202, and the mathematical correspondence constructed in block 204 is the correspondence between the HRV and the running speed. The same procedure applies to the other exertion parameters.

Figure 3:
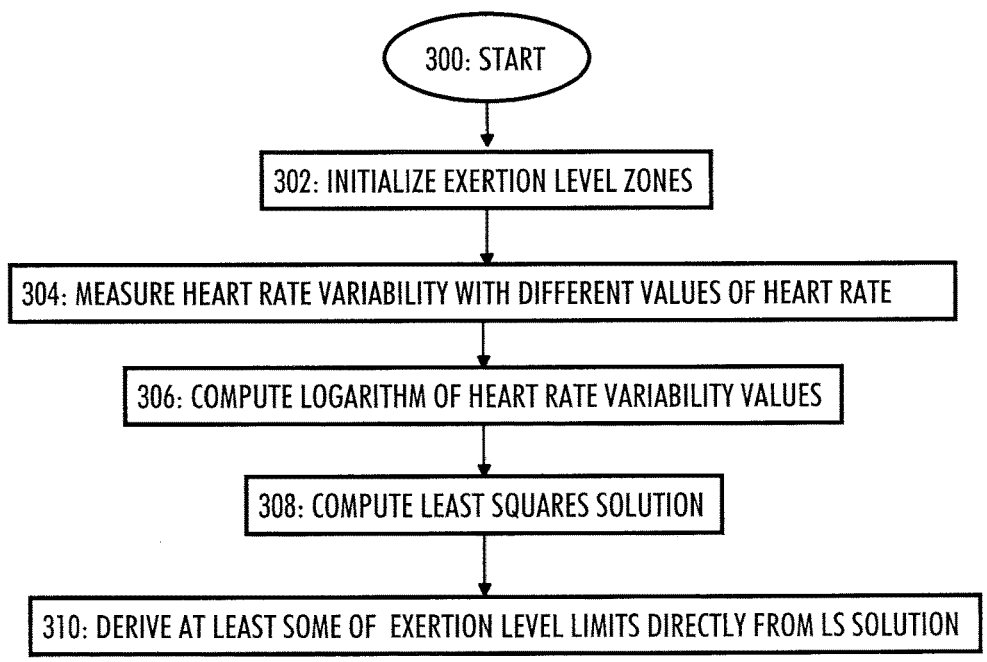
FIG. 3 is a detailed flow diagram of a process for determining the exercise parameters according to an embodiment of the invention.
Figure 6:
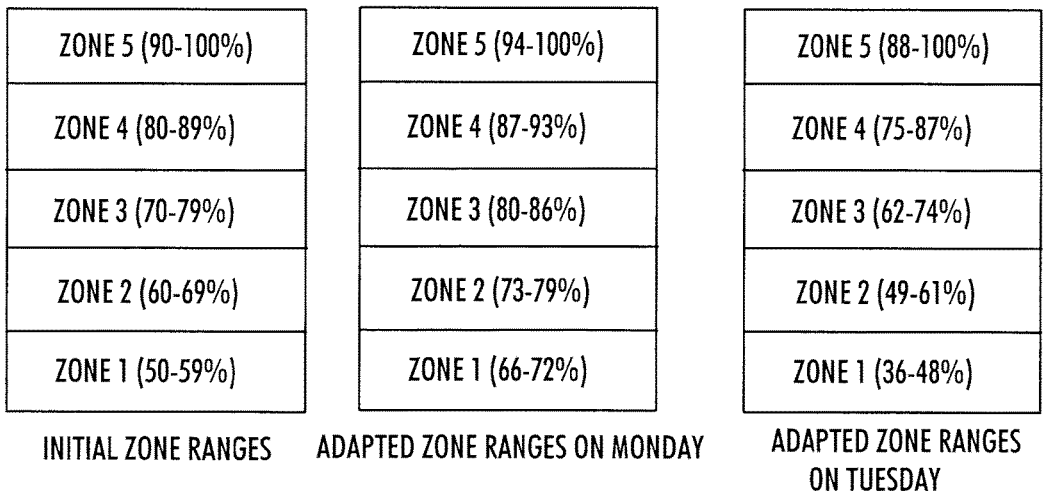
FIG. 6 illustrates exertion level zones before and after adaptation.

Let us now discuss the process of FIG. 2 in greater detail with reference to the flow diagram of FIG. 3. The process starts in block 300, wherein the start may be associated with the user starting a fitness exercise. Let us in this example consider the heart rate as the exertion parameter for the sake of simplicity. In block 302, the exertion level zones are initialized. Polar Sport Zones are an example of the exertion level zones. The initialization may be carried out by the user entering initial exertion level zone limits, or they may have been entered beforehand and stored in a memory unit and retrieved from the memory in block 302 in response to the user commands received through an interface of an apparatus executing the process. FIG. 6 illustrates an example of such exertion level zone ranges, wherein the zone ranges are defined by percentage ranges with respect to the maximum heart rate of the user, e.g. zone 1 contains heart rates between 50% and 59% of the maximum heart rate of the user. The initial or average zone ranges may optionally be customized for the user on the basis of measurements carried out beforehand and, then, stored in the memory unit.

Figure 5:
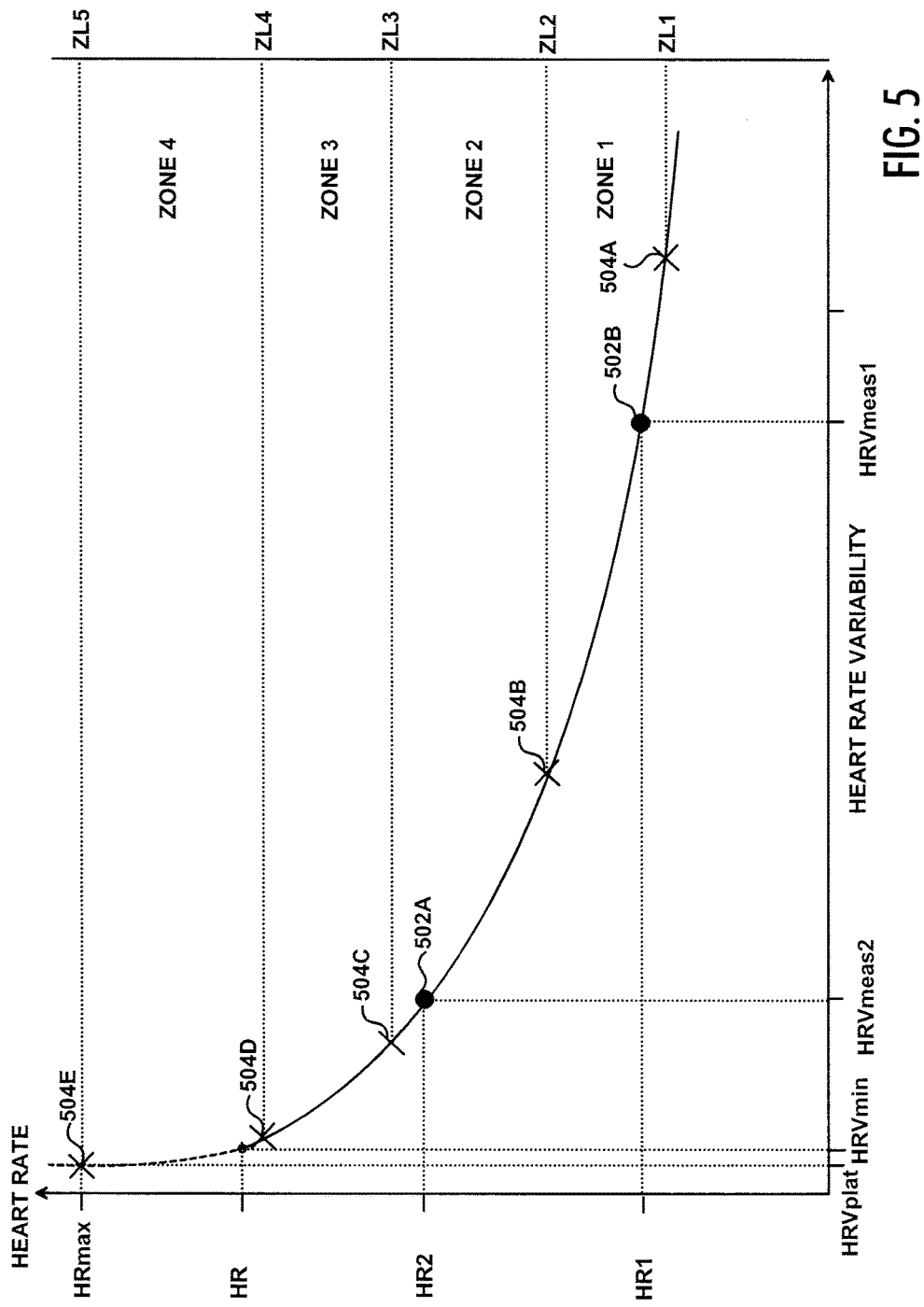
FIG. 5 illustrates correlation between heart rate variability and heart rate and determination of exertion level zones according to an embodiment of the invention.

In block 304, the HRV is measured with different values of the heart rate preferably in the beginning of the exercise. As a consequence, at least one heart rate sensor may be attached to the user to enable heart rate measurements in the beginning and during the exercise. The HRV values and associated heart rates may be stored in a database contained in the memory unit. In many scenarios, the correlation between the heart rate and the HRV follows a logarithmic function with a base of 2. An example, of such a correlation is illustrated in FIG. 5 where the HRV is measured with two heart rates and values denoted by 502A and 502B have been obtained. In practice, more than two measurement points may be acquired and the measured HRV values typically follow roughly the graph of FIG. 5. In block 306, a 2-based logarithm is computed for the HRV values and, since the correlation follows the 2-based logarithm, the HRV values following the graph of FIG. 5 now follow roughly a linear line. Therefore, a least squares (LS) solution may be calculated to derive such a linear line followed by the measured logarithmic HRV values. The actual computation of the LS solution is as such known in the art of signal processing, and the description of that is omitted. The resulting linear line or function now describes the correlation between the logarithmic HRV values and the heart rate.

In block 310, the exertion level zones are adapted to the current physiological state of the user, i.e. to the LS solution. At least some of the limits of the exertion level zones may be derived directly from the LS solution. For example, the lower limit of zone 1 may be selected to be 50% of the current maximum heart rate which is obtained in the LS solution at a point where the HRV is 3.11. Such a value derives from the fact that about 50% of the maximum heart rate is obtained when an SD1 parameter is 8.63 ms, and $\log_2(8.63)=3.11$. 3.11 is a typical value for the 50% heart rate for men, while the corresponding value for women is 3.23, which may be taken into account in the zone adaptation, e.g. the user typically has entered a gender to his exercise apparatus. In addition to the gender, the 50% heart rate obtained from the SD1 parameter may depend on age, and other personal information that may be entered by the user. Instead of SD1 parameters, other corresponding parameters may be used, e.g. HF power or rMSSD (root Mean Square of Successive Differences). The LS solution may also be used to derive a daily maximum heart rate of the user. The 50% heart rate or the maximum heart rate or any other heart rate value thus acquired may be compared with the corresponding heart rate in the initial zone ranges (see FIG. 6). If the heart rate value obtained from the LS solution is higher than the corresponding heart rate in the initial zone ranges, the zone limits may be raised, and if the heart rate value obtained from the LS solution is lower than the corresponding heart rate in the initial zone ranges, the zone limits may be lowered to adapt the zone ranges to the prevailing state of the user. For example, if the 50% heart rate limit in the initial zone ranges is 100 pulses per minute, and the LS solution computed on Monday (central sub-figure in FIG. 6) indicates that the prevailing 50% heart rate lower limit is 110 pulses per minute, i.e. the user is in better physiological state for the exercise than what the initial zone ranges presume, the zone limits may be raised as indicated in the central portion of FIG. 6. In FIG. 6, the maximum heart rate initially stored in the exercise apparatus may be maintained, i.e. the maximum heart rate is not changed to correspond with the prevailing maximum heart rate, and the zone limits may be defined as percentages with respect to the initial maximum heart rate. Thus, the 50% lower limit of zone 1 may be raised to 66%, and the remaining limits may be set so that each zone covers a range of equal size. On the other hand, if the LS solution computed on Tuesday (right hand sub-figure in FIG. 6) indicates that the prevailing 50% heart rate lower limit is 90 pulses per minute, i.e. the user is in exhausted or otherwise in a poorer physiological state for the exercise than what the initial zone ranges presume, the zone limits may be lowered as indicated in the right hand portion of FIG. 6. Thus, the 50% lower limit of zone 1 may be lowered to 36%, and the remaining limits may be set so that each zone covers a range of equal size. Ranges of unequal size are naturally possible, depending on the initial zone ranges, and the process maintains the same pattern of zone sizes. As a consequence, the limits of the heart rate zones are adapted to the prevailing physiological state of the user when compared to the physiological state associated with the initial zone ranges. The physiological states may be determined from the mathematical correspondence, e.g. the LS solution, by determining at which value of the exertion parameter a certain HRV is obtained from a configuration setting the initial zone ranges and from the mathematical correspondence derived in block 202 or 306/308.

Referring to FIG. 5 as another example of setting the zone ranges, the lowest limit of zone 1 representing the lowest zone expected to have training effect may be derived by taking a heart rate value corresponding to a determined HRV value, e.g. 10 ms at point denoted by 504A. The lower limit 504C of zone 3 may also be derived by taking a heart rate value corresponding to a determined, lower HRV value, e.g. 3 ms. The lower limit of zone 3 also defines the higher limit of zone 2, e.g. the lower limit of zone 3 minus 1. The lower limit 504B of zone 2 may be in midpoint between the lower limits of zones 1 and 3 or it may be obtained as the lower limits of zones 1 and 3. The higher limit of zone 4 may be the maximum exertion level at point 504E, e.g. the maximum heart rate which may be calculated with 220 minus user's age or at a determined HRV value HRVplat, from the mathematical model as described above. The lower limit of zone 4 may be obtained from a heart rate with a determined HRV value at point 504D, e.g. 1.5 ms or by extrapolating the mathematical correspondence by using the maximum heart rate as a fitting parameter outside the range of measured heart rate values and/or values of another exertion parameter. In summary, the zone limits may be obtained directly from the mathematical model at determined HRV values and/or derived from the model by processing the model further, e.g. by extrapolating or interpolating the model.

Figure 4:
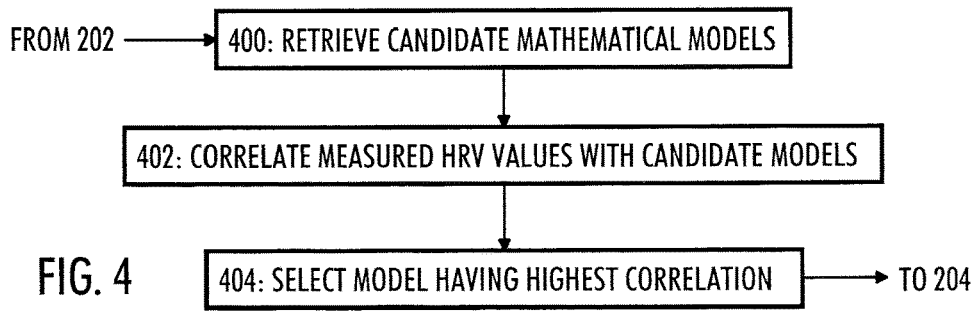
FIG. 4 is a flow diagram illustrating a process for adapting to different measurement environments.

Different exertion parameters correlate with the HRV in a different manner, and even the same exertion parameter, e.g. the heart rate, may correlate with the HRV in a different manner with respect to different users. For example, a logarithmic function with a base different from two may describe the correlation better in some cases. Therefore, the process may have a plurality of candidate models and select a candidate model that provides the best match with the measured HRV and exertion parameter values. FIG. 4 illustrates the process according to this embodiment. The process may be carried out between blocks 202 and 204 of FIG. 2 or between blocks 304 and 306 of FIG. 3. Referring to FIG. 4, the candidate models are retrieved from a memory unit in block 400. With respect to each candidate model, the candidate model is correlated in block 402 with the measured HRV and exertion parameter values, and the result of the correlation is memorized for comparison with corresponding results obtained with respect to the other candidate models. The correlation in the process of FIG. 4 may include a computation of Euclidean distances of the measured values to the line of the LS solution. In other words, logarithms with different bases may be calculated for the measured values, an LS solution may be derived for each logarithmic function, and the Euclidean distances of the measured values to each LS solution may be calculated. Naturally, other models than those based on logarithmic functions may be used. The lowest sum of Euclidean distances of the measured values indicates the highest correlation with the model, and the candidate model having the lowest sum of Euclidean distances is selected in block 404. Providing a plurality of models enables the process to adapt to different environments and types of users, thereby improving the performance and accuracy of the process for determining the physiological state of the user.

In another embodiment of FIG. 4, instead of selecting one of the candidate models, the models may be combined linearly or non-linearly to provide a combined model which is more accurate with respect to the measurements than any individual model. For example, for each measured value a corresponding value from a candidate model having the lowest Euclidean distance to the measured value may be selected. Accordingly, values from different candidate models may be selected for different measured values to form a new set of values for the mathematical correspondence. Then, a new LS solution or another interpolation may be computed for this new set of values, thereby providing a mathematical correspondence that has an improved correlation with the measured values.

The exertion level zones may be used as training instruction targets to define the exercise profile. The exercise profile may define time-line for the training, wherein the time-line comprises a sequence of the exertion level zones and a time target for each zone in the sequence. The same zone may naturally be repeated in the time-line with the same or different time target.

The exertion level zones may also be used for determining a training effect for each exertion level zone by deriving from the mathematical correspondence a factor characterizing the training effect at that exertion level zone with the current physiological state of the user. When the user is tired or exhausted, training at lower exertion level zones (zone 1 or 2) provides a better training effect than training at higher exertion level zones (zones 4 or 5). Thus, a higher weight may be assigned to the lower zones, e.g. zone 1: 0.9; zone 2: 0.8; zone 3: 0.7; zone 4: 0.6; zone 5: 0.5. On the other hand, when the user is well rested and fresh, training at all exertion level zones provides a good training effect. Thus, an equal weighting may be assigned to all zones or even a higher weighting may be assigned to the higher zones. The coefficients may also be determined from the comparison of information obtained from the mathematical correspondence with corresponding information associated with the initial zone ranges, e.g. the 50% heart rate discussed above. If the prevailing 50% heart rate is lower than the initial 50% heart rate, the user is considered to be less adaptive to heart training, and more weight may be put to the lower zones. The training effect may be displayed to the user through a user interface apparatus in real-time.

Figure 7:
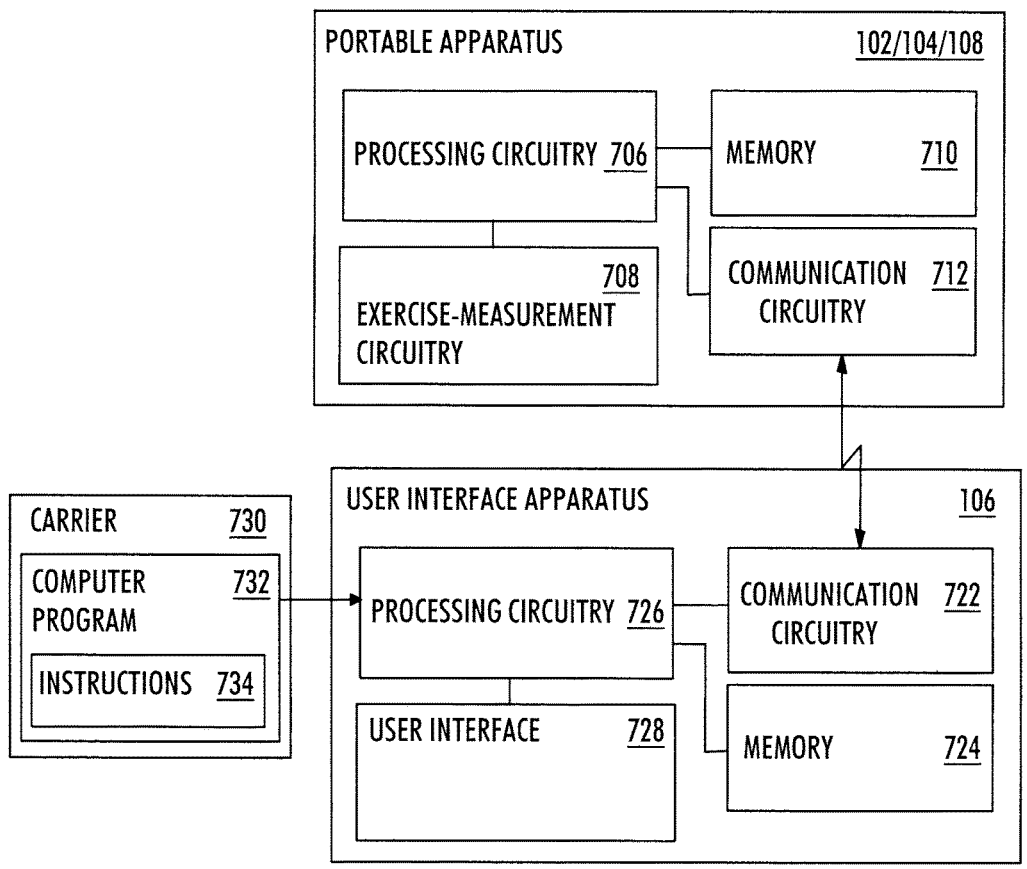
FIG. 7 illustrates apparatuses according to embodiments of the invention.

FIG. 7 illustrates a generic block diagram of a system according to an embodiment of the invention for carrying the above-described processes and functionalities. FIG. 7 illustrates embodiments of apparatuses that may be used to carry out the above-described processes and functionalities. Referring to FIG. 7, an embodiment of the present invention provides a portable apparatus, e.g. one of the accessory devices 102, 104, 108, comprising an exercise-related parameter measurement circuitry 708 configured to measure the exertion parameter values related to the user carrying out an exercise, a communication circuitry 712 configured to provide the portable apparatus with a wireless communication capability, a processing circuitry 706, and a memory 710. The exertion parameter values are measurement data characterizing an exercise, e.g. heart rate, speed, cadence, or other metrics listed above. The exercise-related parameter measurement circuitry 708 may include at least a heart rate measurement circuitry used for determining the HRV of the user. The heart rate measurement circuitry 708 may provide a single or multi-channel ECG signal in the form of a character, such as timing instant, associated with a heart pulse. When the exertion parameter is other than the heart rate, the exercise-related parameter measurement circuitry 708 may comprise another sensor measuring the exertion parameter being used to determine the exertion of the exercise. The other sensor may also be physically separate from the portable apparatus 102, 104, 108 and communicate with the portable apparatus 102, 104, 108 through the communication circuitry 712, e.g. when the heart rate measurement circuitry is attached to the chest of the user and the stride sensor is attached to a user's shoe, for example.

The user may wear the portable apparatus 102, 104, 108 attached to his/her body or clothes and a user interface apparatus 106 around the wrist, for example. However, the user interface apparatus 106 is not limited to that, and it may be a personal computer, a laptop, a personal digital assistant, a mobile phone, a palm device, or another computer device comprising a user interface for presenting the exercise-related measurement data to the user and for applying configuration data to the portable apparatus 102, 104, 108. The user interface apparatus 106 comprises a communication circuitry 722 configured to provide a wireless communication connection with the portable apparatus 102, 104, 108. The user interface apparatus 106 further comprises a user interface 728 enabling interaction with a user of the user interface apparatus 106. The user interface 728 may comprise display and input means as listed above. The user interface apparatus 106 further comprises a processing circuitry 726 configured to communicate with the portable apparatus 102, 104, 108 through the communication circuitry 722 so as to receive exercise-related data from the portable apparatus 102, 104, 108, to present the received processed exercise-related measurement data to the user, to receive configuration data from the user through the input means, and optionally to cause transmission of the configuration data to the portable apparatus 102, 104, 108. In an embodiment, the user interface apparatus 106 comprises the exercise-related parameter measurement circuitry 708, e.g. the heart rate measurement circuitry. Then, the user may not need to wear the portable apparatus at all.

In an embodiment, the processing circuitry 726 is implemented by a digital signal processor, a microcontroller, or another similar controller configurable by computer programs. The user interface apparatus 106 may further comprise a memory 724 for storing such computer programs to be executed by the processing circuitry 726. An embodiment provides a computer program 732 stored on a (transitory or non-transitory) carrier 730 comprising program instructions 734 which, when loaded into the user interface apparatus 106, cause the user interface apparatus 106 to carry out the above-described processes. The carrier may be comprised in the memory unit 724, or it may be a separate storage device or medium. In an embodiment where the portable apparatus 102, 104, 108 is configured to carry out the processes according to embodiments of the invention, the processing circuitry 706 is implemented by a digital signal processor, a microcontroller, or another similar controller configurable by computer programs. The memory 710 may store computer programs 732 comprising the instructions 734 to be executed by the processing circuitry 706. An embodiment provides a computer program comprising program instructions which, when loaded into the processing circuitry 706, cause the portable apparatus 102, 104, 108 to carry out the above-described processes.

The computer program may be in source code form, object code form, or in some intermediate form. The computer program may be stored in the memory or on a carrier which may be any entity or device capable of carrying the program. The carrier may be a computer-readable storage medium. Besides this, the carrier may be implemented as follows, for example: the computer program may be embodied on a record medium, stored in a computer memory, embodied in a read-only memory, carried on an electrical carrier signal, carried on a telecommunications signal, and/or embodied on a software distribution medium. In some jurisdictions, depending on the legislation and the patent practice, the carrier may not be the telecommunications signal.

There are many ways to structure the program. The operations of the program may be divided into functional modules, sub-routines, methods, classes, objects, applets, macros, etc., depending on the software design methodology and the programming language used. In modern programming environments, there are software libraries, i.e. compilations of ready-made functions, which may be utilized by the program for performing a wide variety of standard operations.

Any one of the processing circuitries 706, 726 may be realized by an ASIC (application-specific integrated circuit), but it can be foreseen that the processor is realized by a digital signal processor, a microcontroller, or any other suitable processing unit selected according to required processing capacity, power consumption, etc. When the processing circuitry 706 is a digital signal processor of any kind, the exercise measurement circuitries 708 may include one or more analog-to-digital converters converting the exercise-related measurement data into a digital form.

The wireless communication connection between the portable apparatus and the user interface apparatus may be configured to operate according to the specifications of Bluetooth (or Bluetooth low energy, BTLE), ANT, wireless USB (Universal Serial Bus) or Zigbee (IEEE 802.15.4). In an embodiment, inductive-based technology based on at least one of the following frequencies is used in the wireless communication: 27 kHz, 125 kHz, 131 kHz, 250 kHz, and below 10 kHz, such 5 kHz. The communication circuitries 712, 722 may comprise circuit components necessary for communication according to a wireless communication protocol used between the portable apparatus 102, 104, 108 and the user interface apparatus 106. Accordingly, the wireless communication circuitries may comprises analog-to-digital (A/D) and digital-to-analog (D/A) converters needed to convert analog signals to digital samples and vice versa, amplifiers, frequency-converters, filters and antennas configured according to the specifications of the wireless communication protocol.

In an embodiment, the processing circuitry 706 of the portable apparatus 102, 104, 108 determines the physiological state of the user on the basis of the HRV and the exertion parameter values and monitors the exercise according to the determined physiological state, e.g. by carrying out the adaptation of the exertion level zones and/or by displaying the exertion level to the user. The initial exertion zone ranges may be received as a user input from the user interface apparatus over the wireless connection and through the communication circuitries 722 and 712. The processing circuitry 706 receives the heart rate from the heart rate measurement circuitry 708. When an exertion parameter other than the heart rate is used, the exertion parameter value is also received simultaneously with the heart rate from a corresponding sensor communicating with the processing circuitry. The processing circuitry computes the HRV from the received heart rate at different values of the exertion parameter. The user may be provided with the current value of the exertion parameter continuously through the user interface 728, and the processing circuitry 706 may instruct the user to apply different exertion levels, e.g. different heart rates, so that the HRV may be calculated with different values of the exertion parameter. When sufficient measurements have been carried out, the processing circuitry 706 determines the mathematical correspondence between the exertion parameter and the HRV, adapts the initial exertion level zones, and transmits the adapted exertion level zones to the user interface apparatus 106. The processing circuitry 706 may also compute the coefficients for the exertion level zones to enable determination of the training effect after the exercise and transmit the coefficients to the user interface apparatus through the wireless communication circuitries 712, 722. When the user interface apparatus 106 receives the adapted exertion level zones from the portable apparatus 102, 104, 108, it may indicate to the user readiness to start the exercise and to guide the user throughout the exercise with the adapted exertion level zones, control the exercise according to the exertion level zones, and/or determine the training effect of the exercise on the basis of received coefficients and display the training effect to the user.

In another embodiment, the processing circuitry 726 of the user interface apparatus 106 determines the physiological state of the user and carries out monitoring of the exercise. The procedure is similar to the operation of the processing circuitry 706, but now the initial exertion level zones, the HRV and the exertion parameter values are transferred to the processing circuitry 726, and the processing circuitry 726 computes the mathematical correspondence to determine the physiological state of the user. Accordingly, the processing circuitry 726 may adapt the exertion level zones and/or determine the training effect of the exercise according to the mathematical correspondence, as described above.

In summary, the apparatus according to embodiments of the invention may be a performance monitor, e.g. a wrist device coupled with a heart rate transmitter a wrist device with build-in heart rate detection system, such as that based on optical or mechanical heart rate detection, or a mobile phone or other portable computer system with appropriate wireless interface (BTLE, ANT, or proprietary wireless interface) for receiving heart rate information from a heart rate detector unit. In another embodiment, the apparatus is a printed circuit board with processor capability, and the printed circuit board may have an interface to receive heart rate information from a heart rate detector unit through a wireless interface (BTLE, ANT, or any other wireless interface). In yet another embodiment, the apparatus is a standalone heart rate detector, e.g. a heart rate transmitter with built-in capability to determine the physiological state of the user and to adapt the exertion level limits according to embodiments of the invention or a heart rate data logger with same functionality and equipped with a mass memory for storing the heart rate information. The apparatus may be the processing circuitry 706 or 726 equipped with an interface to the wireless communication circuitry 706 or 726 to provide the apparatus with the wireless communication capability.

As used in this application, the term 'circuitry' refers to all of the following: (a) hardware-only circuit implementations, such as implementations in only analog and/or digital circuitry, and (b) to combinations of circuits and software (and/or firmware), such as (when applicable): (i) a combination of processor(s) or (ii) portions of processor(s)/software including digital signal processor(s), software, and memory (memories) that work together to cause an apparatus to perform various functions, and (c) to circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular element, a baseband integrated circuit or applications processor integrated circuit for a mobile phone or a similar integrated circuit in server, a cellular network device, or other network device.

It should be noted that the Figures illustrate simplified block diagrams that only show some elements and functional entities, all being logical units whose implementation may differ from what is shown. The connections shown in these figures are logical connections; the actual physical connections may be different. Interfaces between the various elements may be implemented with suitable interface technologies. It is apparent to a person skilled in the art that the described apparatuses may also comprise other functions and structures. It should be appreciated that details of some functions, structures, and elements, and the protocols used for communication are irrelevant to the actual invention. Therefore, they need not be discussed in more detail here, because such discussion might blur the invention with unnecessary details. The implementation and features of the apparatuses according to the invention develop rapidly. Such development may require extra changes to the embodiments described above. Therefore, all words and expressions should be interpreted broadly and they are intended to illustrate, not to restrict, the embodiments. Although the apparatuses have been depicted as separate single entities, different parts may be implemented in one or more physical or logical entities. It will be obvious to a person skilled in the art that, as technology advances, the inventive concept can be implemented in various ways. The invention and its embodiments are not limited to the examples described above but may vary within the scope of the claims.

What is claimed is:

1. An apparatus that processes exercise-related measurement data, the apparatus comprising:
   exercise-related parameter measurement circuitry;
   at least one biometric sensor comprising at least one heart activity sensor; and
   a processor configured to cause the apparatus to perform operations comprising:
   acquiring a plurality of heart rate variability values and a plurality of exertion parameter values measured by the at least one heart activity sensor during an exercise using the exercise-related parameter measurement circuitry, wherein the heart rate variability values represent a measure of variation in heart beat intervals and correlate with the exertion parameter values through a human physiological mechanism, and wherein the exertion parameter values characterize physical exertion of the exercise;
   constructing a mathematical correspondence from the plurality of measured heart rate variability values and associated exertion parameter values, the mathematical correspondence describing correlation between the heart rate variability values and the exertion parameter values and describing the user's physiological state during the exercise;
   determining an overall training effect of the exercise by computing, for each of a plurality of exertion level zones, from the mathematical correspondence, a factor characterizing a training effect at that exertion level zone in the user's physiological state during the exercise and determining the overall training effect of the exercise by using the factors, said computing the factor for each of the plurality of exertion level zones comprising:
   a) assigning, when the mathematical correspondence indicates that the user is tired or exhausted, a higher weight to lower exertion level zones than to higher exertion level zones to provide a better training effect on the lower exertion level zones than on the higher exertion level zones; and b) assigning, when the mathematical correspondence indicates that the user is well rested, an equal weighting to all exertion level zones; and outputting the overall training effect of the exercise to the user.

2. The apparatus of claim 1, wherein the operations further comprise monitoring the physical exertion of the exercise by adapting ranges of the plurality of exertion level zones of the exercise to the mathematical correspondence, wherein the ranges of the exertion level zones are defined as exertion parameter values.

3. The apparatus of claim 2, wherein the operations further comprise initializing an exercise profile comprising a plurality of said exertion level zones with different ranges defined as initial values of the exertion parameter values; and changing a range of at least one exertion level zone by changing at least one initial value of the exertion parameter value of said at least one exertion level zone on the basis of the constructed mathematical correspondence.

4. The apparatus of claim 2, wherein the apparatus further comprises a user interface comprising a display unit, and wherein the operations further comprise causing the apparatus to display at least one range of the plurality of exertion level zones to the user.

5. The apparatus of claim 2, wherein the operations further comprise adapting the range of the at least one exertion level zone by acquiring, using the mathematical correspondence, an adapted exertion parameter value associated with a predetermined different heart rate variability value, which has not been measured from the user, and using the adapted exertion parameter value to define the range, and by setting the exertion parameter value as an upper limit or a lower limit of the at least one exertion level zone.

6. The apparatus of claim 1, wherein said exertion parameter level includes a level of at least one of the following exertion parameters: heart rate, speed of motion, pedaling power, and motion intensity.

7. The apparatus of claim 1, wherein the operations further comprise causing the apparatus to construct the mathematical correspondence by providing a plurality of different candidate mathematical correspondence models, by determining correlation between the acquired heart-rate variability values and said plurality of different candidate mathematical correspondence models, and by selecting a mathematical correspondence model having the highest correlation with the acquired heart-rate variability values.

8. The apparatus of claim 1, wherein the apparatus further comprises a user interface comprising a display unit, and wherein the operations further comprise causing the apparatus to input an exertion parameter value, and to display the exertion parameter value to the user along with a reference exertion parameter value obtained from the mathematical correspondence.

9. The apparatus of claim 1, wherein the operations further comprise causing the apparatus to monitor the physical exertion of the exercise by determining a target heart rate variability value or a target heart rate variability range for the exercise, by obtaining, from the mathematical correspondence, a target exertion parameter level or range corresponding to the target heart rate variability value or range, and by instructing the user to achieve the target exertion parameter level or range.

10. The apparatus of claim 1, wherein the apparatus further comprises:

a memory module configured to store the overall training effect; and processing circuitry configured to adapt at least one of the plurality of exertion level zones based on the stored overall training effect, and to generate an output indicating adaptation of the at least one of the plurality of exertion level zones based on the stored overall training effect.

11. A computer program product embodied on a non-transitory distribution medium comprising a set of computer program instructions that, when executed by a processor, cause the processor to perform operations comprising:

acquiring a plurality of heart rate variability values and a plurality of exertion parameter values measured by at least one heart activity sensor during an exercise using exercise-related parameter measurement circuitry, wherein the heart rate variability values represent a measure of variation in heart beat intervals and correlate with the exertion parameter values through a human physiological mechanism, and wherein the exertion parameter values characterize physical exertion of the exercise;

constructing a mathematical correspondence from the plurality of measured heart rate variability values and associated exertion parameter values, the mathematical correspondence describing correlation between the heart rate variability values and the exertion parameter values and describing the user's physiological state during the exercise;

determining an overall training effect of the exercise by computing, for each of a plurality of exertion level zones, from the mathematical correspondence, a factor characterizing a training effect at that exertion level zone in the user's physiological state during exercise and determining the overall training effect of the exercise by using the factors, said computing the factor for each of the plurality of exertion level zones comprising:

a) assigning, when the mathematical correspondence indicates that the user is tired or exhausted, a higher weight to lower exertion level zones than to higher exertion level zones; and b) assigning, when the mathematical correspondence indicates that the user is well rested, an equal weighting to all exertion level zones; and outputting the overall training effect of the exercise to the user.

12. A method of processing exercise-related measurement data in an apparatus, the method comprising:

acquiring a plurality of heart rate variability values and a plurality of exertion parameter values measured by at least one heart activity sensor during an exercise using exercise-related parameter measurement circuitry, wherein the heart rate variability values represent a measure of variation in heart beat intervals and correlate with the exertion parameter values through a human physiological mechanism, and wherein the exertion parameter values characterize physical exertion of the exercise;

constructing a mathematical correspondence from the plurality of measured heart rate variability values and associated exertion parameter values, the mathematical correspondence describing correlation between the heart rate variability values and the exertion parameter values and describing the user's physiological state during the exercise;

determining an overall training effect of the exercise by computing, for each of a plurality of exertion level zones, from the mathematical correspondence, a factor characterizing a training effect at that exertion level zone in the user's physiological state during the exercise and determining the overall training effect of the exercise by using the factors, said computing the factor for each of the plurality of exertion level zones comprising:

a) assigning, when the mathematical correspondence indicates that the user is tired or exhausted, a higher weight to lower exertion level zones than to higher exertion level zones; and
b) assigning, when the mathematical correspondence indicates that the user is well rested, an equal weighting to all exertion level zones; and outputting the overall training effect of the exercise to the user.

* * * * *